US010584309B2

(12) United States Patent
Fadell et al.

(10) Patent No.: US 10,584,309 B2
(45) Date of Patent: Mar. 10, 2020

(54) PRESSURE TRANSDUCER FOR SINGLE-USE CONTAINERS

(71) Applicant: Rosemount Inc., Shakopee, MN (US)

(72) Inventors: Paul R. Fadell, Cypress, TX (US); Michael Knopf, East Wenatchee, WA (US); Jay I. Scheldorf, Bleiblerville, TX (US)

(73) Assignee: Rosemount Inc., Shakopee, MN (US)

( * ) Notice: Subject to any disclaimer, the term of this patent is extended or adjusted under 35 U.S.C. 154(b) by 144 days.

(21) Appl. No.: 15/603,932

(22) Filed: May 24, 2017

(65) Prior Publication Data

US 2018/0223242 A1 Aug. 9, 2018

Related U.S. Application Data (60) Provisional application No. 62/455,052, filed on Feb. 6, 2017.

(51) Int. Cl.
*C12M 1/34* (2006.01)
*C12M 1/00* (2006.01)
(Continued)

(52) U.S. Cl.
CPC ............ *C12M 41/40* (2013.01); *C12M 23/28* (2013.01); *C12M 41/48* (2013.01); *G01L 9/0051* (2013.01);
(Continued)

(58) Field of Classification Search
None
See application file for complete search history.

(56) References Cited

U.S. PATENT DOCUMENTS 1,786,101 A 12/1930 Welch et al.
3,374,674 A 3/1968 Schwartzman
(Continued)

FOREIGN PATENT DOCUMENTS

EP 0399227 A1 11/1990
EP 0753737 A2 1/1997
(Continued)

OTHER PUBLICATIONS

International Search Report and Written Opinion dated Jun. 22, 2018, for International Patent Application No. PCT/US2018/014961, 14 pages.
(Continued)

*Primary Examiner* — Natalie Huls
*Assistant Examiner* — Jermaine L Jenkins
(74) *Attorney, Agent, or Firm* — Christopher R. Christenson; Kelly, Holt & Christenson PLLC (57) ABSTRACT

A pressure-sensing system is presented. The pressure-sensing system comprises a single-use container. The pressure-sensing system comprises a disposable process connector configured to couple directly to the single-use container. The disposable process connector has a deflectable diaphragm. The pressure-sensing system comprises a pressure transducer. The pressure transducer is removably coupled to the disposable process connector. The pressure transducer comprises an isolation diaphragm positioned adjacent the deflectable diaphragm of the disposable process connector. The pressure transducer comprises a pressure sensor module operably coupled to the isolation diaphragm. The pressure transducer also comprises a controller coupled to the pressure sensor. The controller is configured to transmit a detected indication of pressure within the single-use container. A pressure transducer for a single-use container includes a polymeric housing and a base having an isolation diaphragm. A sensor module is coupled to the base, and has a pressure sensor operably coupled to the isolation diaphragm. Circuitry is disposed within the polymeric housing and coupled to the pressure transducer. The circuitry includes a microprocessor configured to obtain a pressure measurement from the pressure sensor and provide an output signal based on the measured pressure.

18 Claims, 12 Drawing Sheets

(51) Int. Cl.
  *C12M 1/36* (2006.01)
  *G01L 9/00* (2006.01)
  *G01L 19/02* (2006.01)
  *G01L 19/08* (2006.01)
  *G01L 19/14* (2006.01)

(52) U.S. Cl.
  CPC ............ *G01L 19/02* (2013.01); *G01L 19/086* (2013.01); *G01L 19/147* (2013.01)

(56) References Cited

U.S. PATENT DOCUMENTS

| | | | |
|---|---|---|---|
| 3,821,897 A | 7/1974 | Frazel | |
| 4,263,115 A | 7/1981 | Kessler et al. | |
| 4,294,124 A | 10/1981 | Kalwaitis | |
| 4,297,871 A | 11/1981 | Wright | |
| 4,305,286 A | 12/1981 | Beuth et al. | |
| 4,599,906 A | 7/1986 | Freud et al. | |
| 4,989,456 A | 2/1991 | Stupecky | |
| 5,460,049 A | 10/1995 | Kirsch | |
| 5,481,920 A * | 1/1996 | Nara ................... | G01L 9/0055 73/720 |
| 5,595,939 A | 1/1997 | Otake et al. | |
| 5,993,395 A * | 11/1999 | Shulze ................ | A61B 5/0215 600/486 |
| 6,050,145 A | 4/2000 | Olson | |
| 6,602,401 B1 | 8/2003 | Feng | |
| 6,894,502 B2 | 5/2005 | Feng et al. | |
| 6,979,307 B2 | 12/2005 | Beretta | |
| 7,252,009 B2 * | 8/2007 | Kosh ................... | G01L 9/0051 73/753 |
| 7,258,017 B1 | 8/2007 | Hedtke | |
| 7,924,017 B2 | 4/2011 | Ammann et al. | |
| 7,972,495 B1 | 7/2011 | Millar et al. | |
| 8,123,397 B2 * | 2/2012 | Baumfalk ............ | B01F 7/162 366/152.1 |
| 8,252,582 B2 | 8/2012 | Baumfalk et al. | |
| 8,304,231 B2 | 11/2012 | Roll | |
| 8,640,560 B2 | 2/2014 | Burke | |
| 8,828,202 B2 * | 9/2014 | Feng ................... | G01N 27/404 204/403.02 |
| 8,900,855 B2 | 12/2014 | Feng et al. | |
| 9,029,130 B2 | 5/2015 | Feng et al. | |
| 9,239,114 B2 | 1/2016 | Lee | |
| 9,267,100 B2 | 2/2016 | Selker et al. | |
| 9,335,000 B2 * | 5/2016 | Selker ................ | F16L 58/185 |
| 9,562,819 B2 * | 2/2017 | Fadell ................. | G08C 17/02 |
| 10,226,076 B2 * | 3/2019 | Althorpe ............ | A24F 47/008 |
| 2001/0028865 A1 | 10/2001 | Cummings et al. | |
| 2002/0072084 A1 | 6/2002 | Meserol et al. | |
| 2003/0168403 A1 | 9/2003 | Corcho-Sanchez et al. | |
| 2004/0027912 A1 | 2/2004 | Bibbo et al. | |
| 2004/0140211 A1 | 7/2004 | Broy et al. | |
| 2005/0163667 A1 | 7/2005 | Krause | |
| 2005/0193825 A1 | 9/2005 | Otsuka | |
| 2005/0256447 A1 | 11/2005 | Richardson et al. | |
| 2006/0228804 A1 | 10/2006 | Xu et al. | |
| 2007/0151349 A1 | 7/2007 | Schumacher et al. | |
| 2007/0185680 A1 | 8/2007 | Kambe et al. | |
| 2007/0252290 A1 | 11/2007 | Teremtiev et al. | |
| 2007/0272027 A1 | 11/2007 | Hedtke | |
| 2008/0032389 A1 | 2/2008 | Selker et al. | |
| 2008/0274541 A1 | 11/2008 | Selker et al. | |
| 2009/0130704 A1 | 5/2009 | Gyure | |
| 2009/0139298 A1 | 6/2009 | Klees et al. | |
| 2010/0017159 A1 | 1/2010 | Burke | |
| 2010/0302008 A1 | 12/2010 | Engelstad et al. | |
| 2011/0187388 A1 | 8/2011 | Ossart | |
| 2011/0201100 A1 | 8/2011 | Proulx | |
| 2011/0249526 A1 | 10/2011 | Wong | |
| 2012/0016603 A1 | 1/2012 | Martin et al. | |
| 2012/0240686 A1 | 9/2012 | Blomberg et al. | |
| 2012/0242993 A1 | 9/2012 | Schick et al. | |
| 2012/0244609 A1 * | 9/2012 | Selker ................ | C12M 23/00 435/288.7 |
| 2012/0290268 A1 | 11/2012 | Bey | |
| 2012/0291238 A1 | 11/2012 | Frej et al. | |
| 2013/0055821 A1 | 3/2013 | Bentley | |
| 2013/0145818 A1 | 6/2013 | Allgauer et al. | |
| 2014/0207016 A1 | 7/2014 | Addington | |
| 2015/0030514 A1 | 1/2015 | Feltham | |
| 2015/0283279 A1 | 10/2015 | Lott | |
| 2015/0316528 A1 | 11/2015 | Schumacher | |
| 2016/0091383 A1 | 3/2016 | Hoffman et al. | |
| 2016/0298068 A1 | 10/2016 | Schumacher et al. | |
| 2018/0179486 A1 * | 6/2018 | Fadell ................. | C12M 23/28 |

FOREIGN PATENT DOCUMENTS

| | | |
|---|---|---|
| EP | 2065701 A2 | 6/2009 |
| GB | 2364125 A | 1/2002 |
| JP | 2008-039523 A | 2/2008 |
| JP | 2009-519440 A | 5/2009 |
| WO | 1992/001218 A1 | 1/1992 |
| WO | 2009/017765 A1 | 2/2009 |
| WO | 2009/146323 A1 | 12/2009 |
| WO | 2013/034891 A1 | 3/2013 |
| WO | 2013/162394 A1 | 10/2013 |
| WO | 2008/016411 A1 | 2/2018 |

OTHER PUBLICATIONS

"90 | Wireless Monitoring Solution for Stackable Totes/Tanks", TankLink, a Division of Telular Corporation, available at www.TankLink.com, Copyright 2012 (2 pages).

"90 | Wireless Monitoring Solution for Highly Corrosive Chemicals", TankLink, a Division of Telular Corporation, available at www.TankLink.com, Copyright 2013 (2 pages).

First Office Action for Chinese Patent Application No. 201510197804.X, dated Jan. 26, 2017, 21 pages including English translation.

Patent Examination Report No. 1 for Australian Patent Application No. 2015253275, dated Nov. 15, 2016, 4 pages.

International Preliminary Report on Patentability for International Patent Application No. PCT/US2015/028192, dated Nov. 17, 2016, 15 pages.

Office Action for Canadian Patent Application No. 2818943, dated Jul. 30, 2014, 2 pages.

International Search Report and Written Opinion for International Patent Application No. PCT/US2015/028192, dated Jul. 27, 2015, 18 pages.

International Search Report and Written Opinion from International Patent Application No. PCT/US2011/065032, dated Apr. 26. 2012, 16 pages.

International Search Report and Written Opinion from International Patent Application No. PCT/US2011/065033, dated Mar. 19, 2012, 16 pages.

Pharmaceutical Industry Solutions; Reliable Liquid Analysis, Brochure by Rosemount Analytical, Emerson Process Management, dated 2005, 12 pages.

S. Schmitmeir et al. Development and Characterization of a Small-Scale Bioreactor Based on a Bioartificial Hepatic Culture Model for Predictive Pharmacological In Vitro Screenings, Biotechnology and Bioengineering. vol. 95, No. 6, dated Dec. 20. 2006, 10 pages.

Application Data Sheet, Tighter pH Control in Pharmaceutical Applications, Jan. 2008, by Rosemount Analytical, Emerson Process Management, 2 pages.

International Search Report and Written Opinion for PCT/US2016024859, dated Jul. 12, 2016, 11 pages.

International Search Report and Written Opinion for PCT/US2016/028884, dated Jul. 28, 2016, 16 pages.

International Search Report and Written Opinion for PCT/US2016/064125, dated Mar. 13, 2017, 16 pages.

Related U.S. Appl. No. 15/278,766, "Single-Use Bioreactor Sensor Interface" filed Sep. 28, 2016, 18 pages.

Related U.S. Appl. No. 15/072,128, "Flow Measurement System for Single-Use Containers", filed Mar. 16, 2016, 15 pages.

Second Office Action for Chinese Patent Application No. 201180059710.06, dated Aug. 22, 2014, 12 pages with English translation.

(56) References Cited

OTHER PUBLICATIONS

Office Action for Chinese Patent Application No. 201180059710.06, dated Feb. 24, 2014, 12 pages with English translation.
Theory and Practice of pH Measurement, PN 44-6033/rev. D, dated Dec. 2010 by Rosemount Analytical, Emerson Process Management, 40 pages.
First Office Action for Chinese Patent Application No. 201210085580.X, dated Jun. 11, 2014, 14 pages including English translation.
"A low-cost system for real time monitoring and assessment of potable water quality at consumer sites", 2013 IEEE Sensors, IEEE, Oct. 28, 2012, pp. 1-4.
International Search Report and Written Opinion for International Patent Application No. PCTUS2017/019563, dated May 25, 2017, 13 pages.
Office Action for Japanese Patent Application No, 2016-565389, dated Sep. 19, 2017, 7 pages including English translation.
Second Office Action for Chinese Patent Application No. 201510197804.X, dated Sep. 29, 2017, 13 pages including English translation.
First Chinese Office Action dated Nov. 29. 2019, for Chinese Patent Application No. 201710674947.1, 16 pages including English translation.

* cited by examiner

PRESSURE TRANSDUCER FOR SINGLE-USE CONTAINERS

CROSS-REFERENCE TO RELATED APPLICATIONS

The present application is based on and claims the benefit of U.S. Provisional Patent Application Ser. No. 62/455,052 filed Feb. 6, 2017, the content of which is hereby incorporated by reference in its entirety.

BACKGROUND

Containers are useful for generating and supporting biological reactions for any number of purposes. Biological reactions can be susceptible to changes in temperature and/or pressure. Moreover, as the biological reaction progresses, the reaction itself may change various parameters within the bioreaction vessel, such as pressure.

The life sciences industry is moving from large capital intensive facilities made of stainless steel with large clean in place (CIP) infrastructure to smaller facilities that use polymer bags or containers functioning as the containers. The container is used once and then disposed. This single-use container technique significantly reduces the capital cost of the plant. For example, in existing facilities that use stainless steel CIP infrastructure, up to 90% of the cost of operating the facility may be due to the clean in place infrastructure, including very high end instrumentation designed to withstand a steam cleaning cycle. By moving to disposable single-use container bags, the CIP portion of the capital can be eliminated and the facility can be more flexible and much smaller, which, in turn, allows for the production of smaller batches that are needed for more targeted drug therapies and other small scale applications. Providing an instrumentation architecture that facilitates the use and adoption of disposable single-use bioreaction techniques would be of significant benefit to the life sciences industry, as well as other industries and processes that generate such biological reactions.

SUMMARY

A pressure-sensing system is presented. The pressure-sensing system comprises a single-use container. The pressure-sensing system comprises a disposable process connector configured to couple directly to the single-use container. The disposable process connector has a deflectable diaphragm. The pressure-sensing system comprises a pressure transducer. The pressure transducer is removably coupled to the disposable process connector. The pressure transducer comprises an isolation diaphragm positioned adjacent the deflectable diaphragm of the disposable process connector. The pressure transducer comprises a pressure sensor module operably coupled to the isolation diaphragm. The pressure transducer also comprises a controller coupled to the pressure sensor. The controller is configured to transmit a detected indication of pressure within the single-use container.

A pressure transducer for a single-use container includes a polymeric housing and a base having an isolation diaphragm. A sensor module is coupled to the base, and has a pressure sensor operably coupled to the isolation diaphragm. Circuitry is disposed within the polymeric housing and coupled to the pressure transducer. The circuitry includes a microprocessor configured to obtain a pressure measurement from the pressure sensor and provide an output signal based on the measured pressure.

DETAILED DESCRIPTION OF ILLUSTRATIVE EMBODIMENTS

Accurate pressure transducers and/or transmitters are typically relatively heavy and cannot interface easily and cost effectively with single-use bioprocessing equipment, such as polymer film containers. Such pressure transducers often require a permanent mounting within a facility. Disposable pressure transducers, on the other hand, have been purpose-built for the single-use industry and are light and made from polymers. However, these disposable pressure transducers do not provide the performance quality of the heavier, accurate pressure transducers. For example, disposable pressure transducers are known to drift over time, or otherwise exhibit inaccuracies.

Embodiments provided herein leverage components, technology and techniques typically used with the heavier, accurate pressure transducers to provide a new pressure transducer that is able to couple directly to a single-use container, such as a bioreaction bag. In one embodiment, core technology from a reliable and accurate pressure transducer is repackaged to achieve significant weight reduction and accuracy, in a very small form factor, with a polymeric housing that may be mounted directly to a single-use vessel, such as a plastic bioreaction bag. Additionally, in some examples, communication with the improved pressure transducer is performed wirelessly.

Figure 1A:
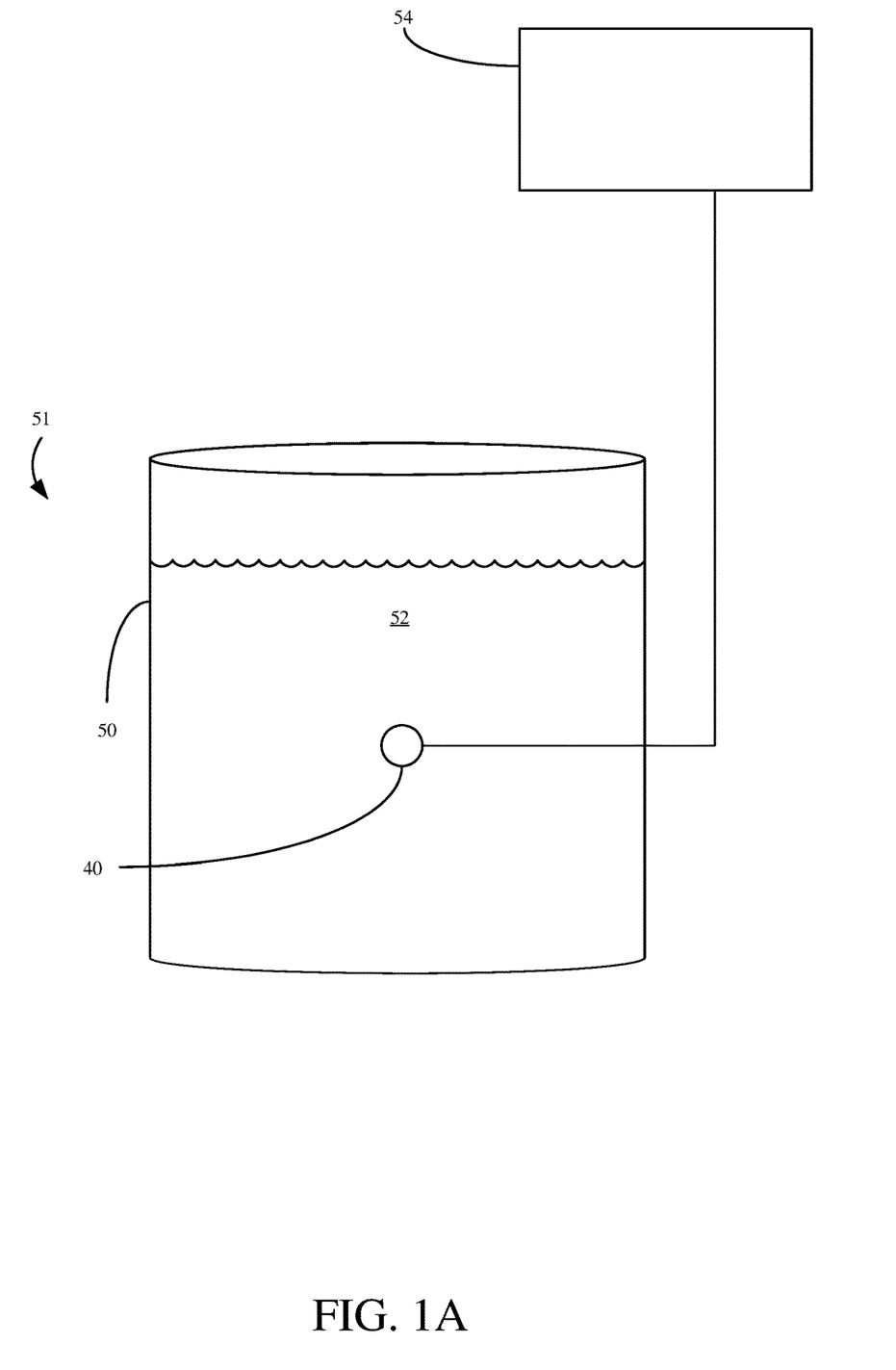
FIG. 1A is a diagrammatic view of a single-use container in which embodiments of the present invention may be useful.

FIG. 1A is a diagrammatic view of a sensor measuring a process variable of a specimen within a single-use container, in which embodiments of the present invention may be useful. Pressure sensor module 40 is electrically coupled to analyzer or controller 54, which may be any suitable analyzer or other electrical instrument or control system. Pressure sensor module 40 is physically coupled to wall 50 of single-use container 51, for example a fermenter. A sample 52 is disposed within single-use container 50 and is monitored, or otherwise measured, by pressure sensor module 40. Embodiments of the present invention generally include a number of configurations in which a pressure sensor module can be used effectively with a single-use container.

Figure 1B:
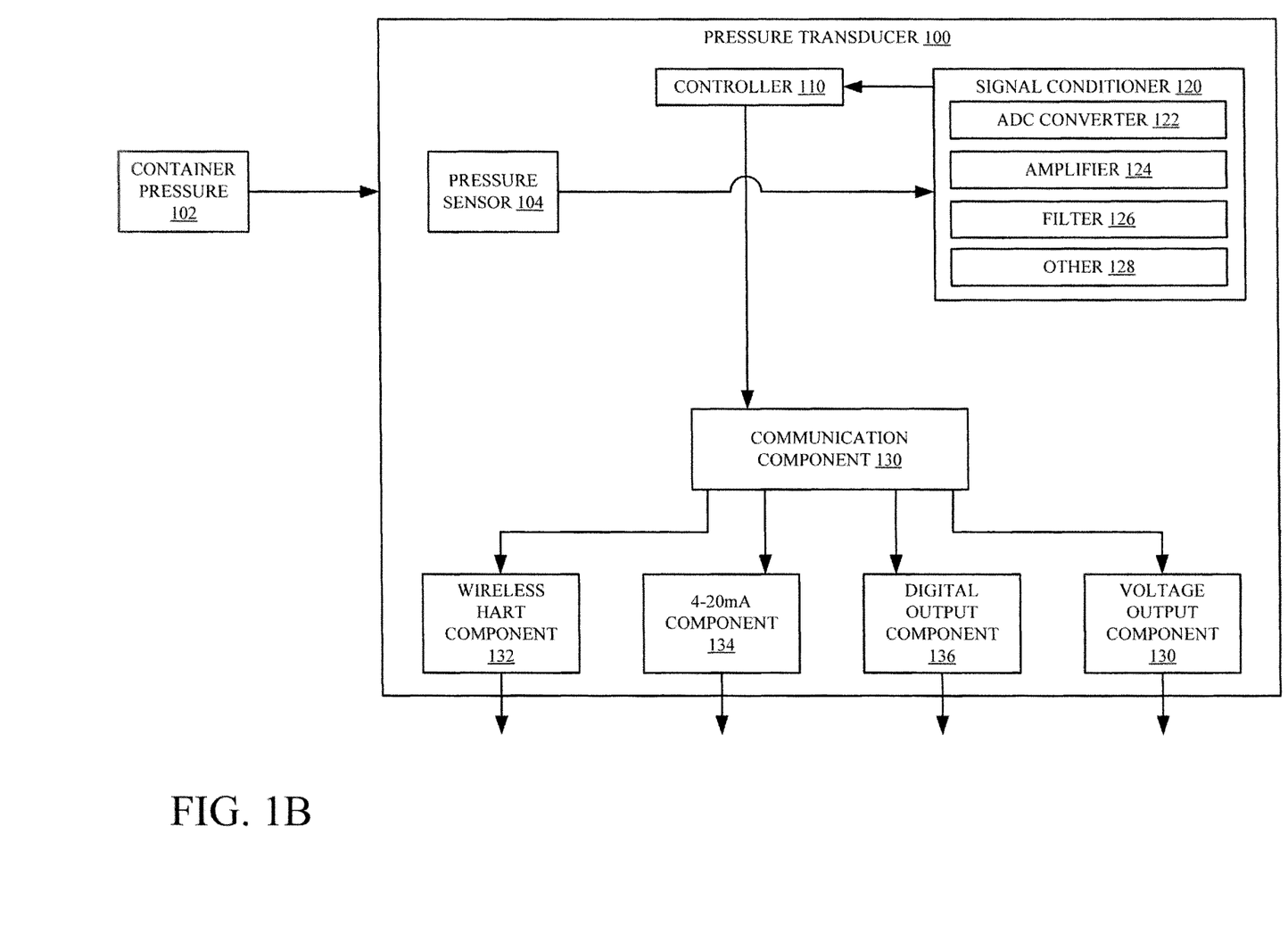
FIG. 1B is a block diagram of a compact pressure transducer in accordance with an embodiment of the present invention.

FIG. 1B illustrates a block diagram of a compact pressure transducer 100 in accordance with an embodiment of the present invention. Transducer 100 preferably provides a signal communication output, for example a WirelessHART communication output in accordance with IEC 62591, as provided by component 132. The signal communication output may also comprise other types of outputs such as a 4-20 mA output (provided by component 134), FOUNDATION™ Fieldbus (provided component 136), and/or a voltage output (provided by component 138).

Pressure transducer 100, comprises a pressure sensor 104 coupled to signal conditioning module 120, which is coupled to a controller 110. Signal conditioning module 120 may comprise an analog-to-digital converter 122 configured to convert an analog sensor signal to a digital representation. Signal conditioning module 120 may also comprise an amplifier 124, configured to amplify one or more signals received. Signal conditioner 120 may include one or more filters 126 and/or other signal conditioning functionality 128. The protocols illustrated in FIG. 1B are understood to be illustrative of suitable protocols only. Other suitable protocols, such as wired HART, NFC, Bluetooth LE, and WIFI are also envisioned, as well as other suitable protocols.

Pressure sensor 104 is preferably a highly accurate solid-state strain gauge pressure sensor. A pressure sensor module including a compact pressure transducer, such as those described herein, can be welded directly to a metal, weight optimized, minimal process interface with a hydraulic transfer fluid fill and final isolating diaphragm of very high sensitivity. The electronics and polymeric housing are highly miniaturized as compared to previously used, permanently mounted pressure sensor module installations. The primary interface between the pressure transducer and the single-use container is a single-use process connector that conveys pressure to the transducer but seals it from the contents of the container to allow the transducer to be a reusable component of a pressure measurement system for a container.

Figure 2A:
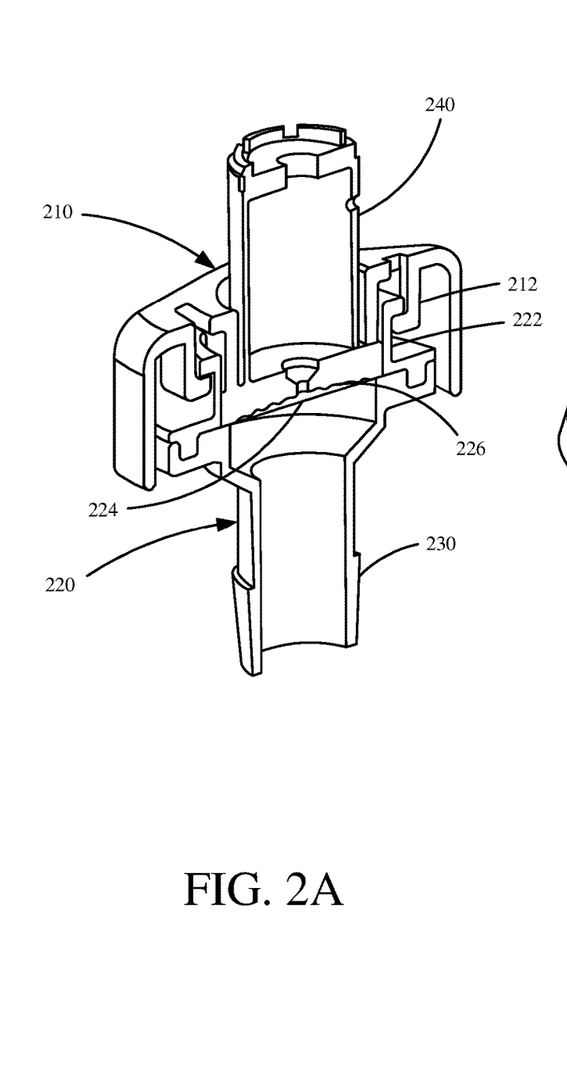
FIGS. 2A-2C illustrate a compact pressure transducer and disposable process connector in accordance with an embodiment of the present invention.
Figure 2B:
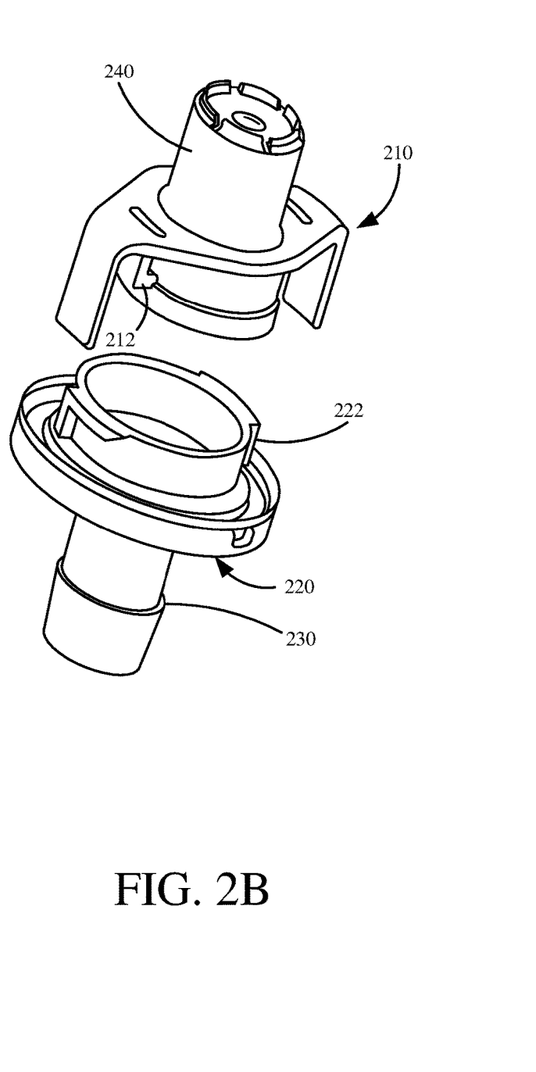
Figure 2C:
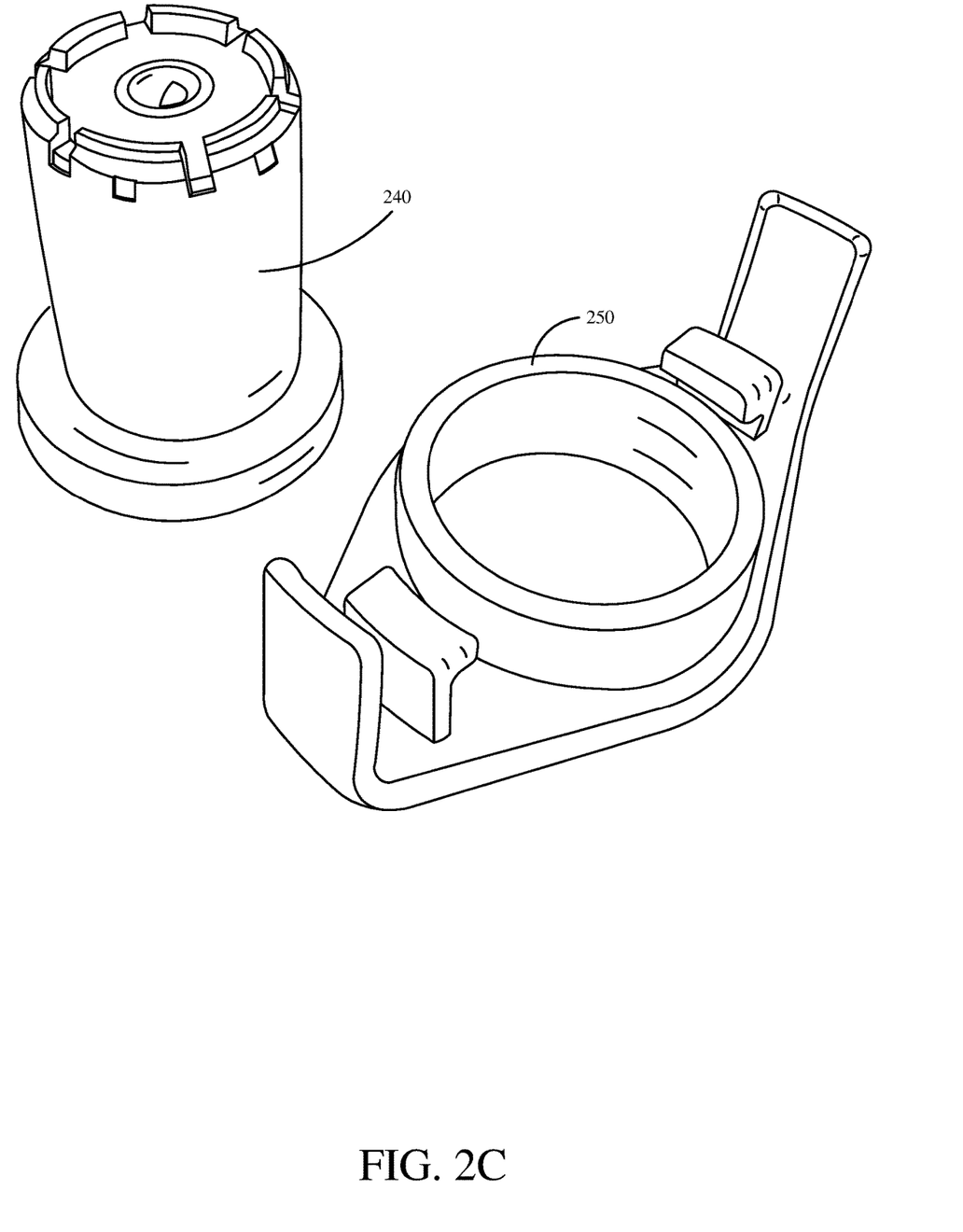

FIGS. 2A-2C are diagrammatic views of a compact pressure transducer and disposable process connector in accordance with an embodiment of the present invention. Transmitter 200 comprises a transmitter housing 210 that is configured to couple to a process connector 220 using coupling features 212 and 222. Coupling features 212 and 222 comprise corresponding fittings configured to removably receive one another, as illustrated in FIGS. 2A and 2B. A length of tubing (not shown) preferably extends over fitting 230, which can be a hose barb fitting. Disposable process connector 220 has a polymeric diaphragm 224 that provides a seal to a container, but moves in response to pressure. Transducer 210 has a diaphragm 226 that is placed in contact with diaphragm 224 when transducer 210 is mounted to disposable process connector 220. Transducer 210 comprises a metal diaphragm. Accordingly, as the pressure within the container changes, both diaphragms move, and the movement is conveyed to a solid-state strain gauge pressure sensor (not shown) within transducer 210, which detects the movement as a pressure signal.

As shown in FIG. 2B, transducer 210 may be coupled to process connector 220 by axially displacing transducer 210 towards disposable process connector 220. Partial rotation causes coupling features 222 and 212 to engage locking process connector 220 to transducer 210. In one example, coupling features 222 and 212 comprise an L-shaped ledge configured to lock transducer 210 to process connector 220.

FIG. 2C is a perspective view of a housing 240 and clamping assembly 250, for transducer 210. As shown in FIG. 2C, a clamping assembly 250 is shown removed from the transducer 210 to better illustrate coupling features 212, described above. Housing 240 is cylindrical preferably with a diameter of about 1 inch. Clamping assembly 250 is configured to slide over body 240 of transducer 210 to couple to a disposable process connector, such as connector 220.

Figure 3A:
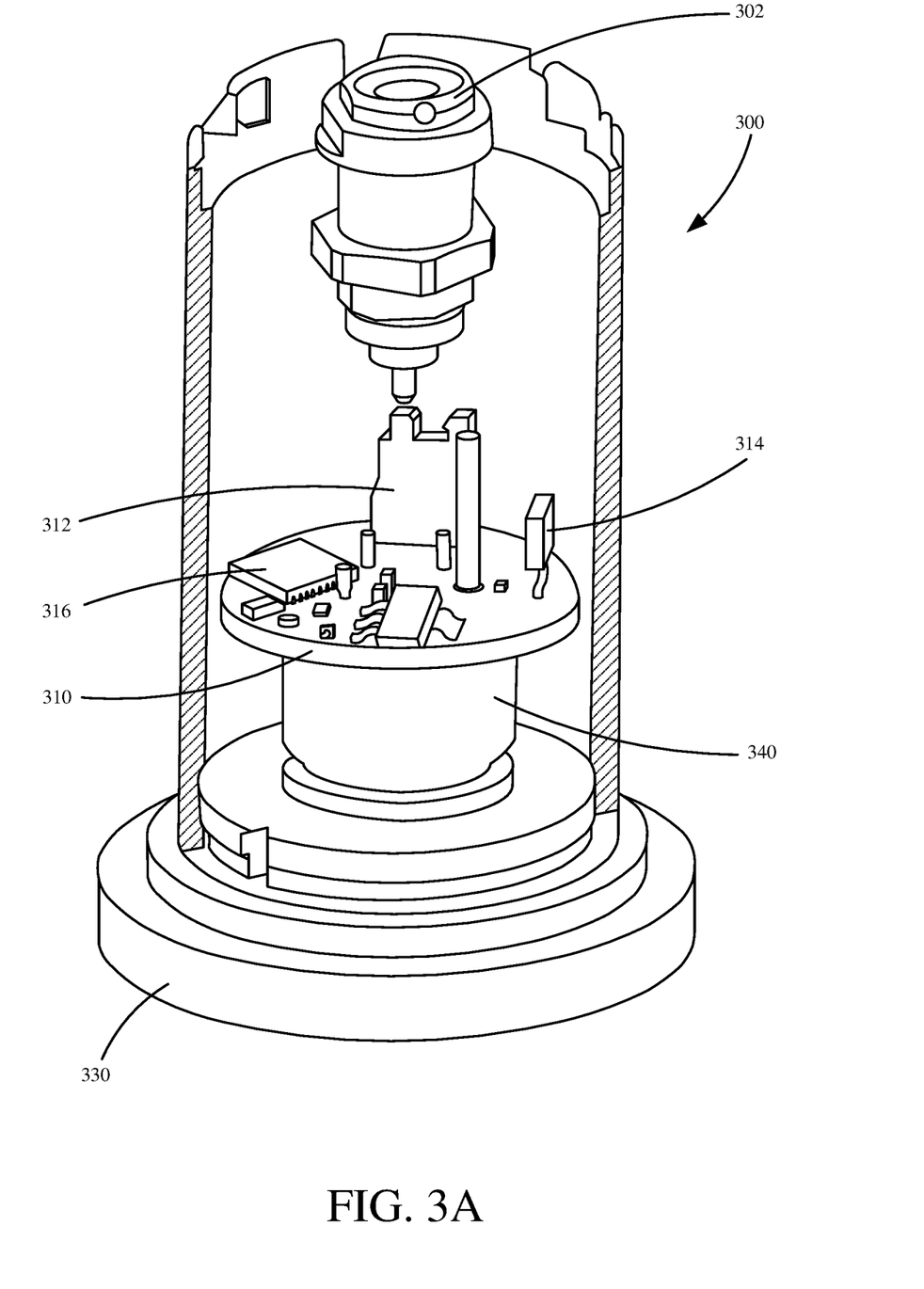
FIGS. 3A-3C illustrate views of a pressure transducer housing and circuitry in accordance with an embodiment of the present invention.
Figure 3B:
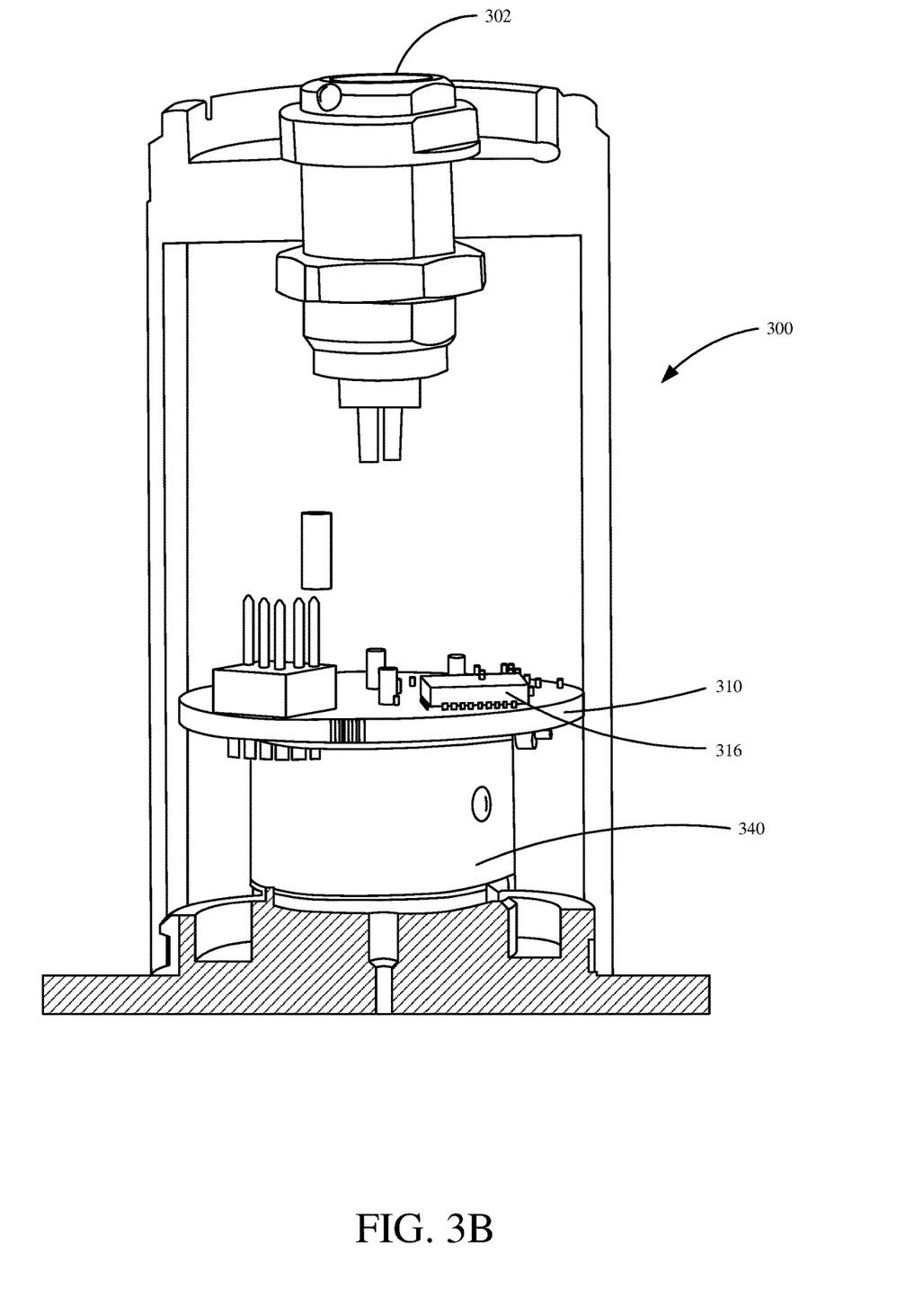
Figure 3C:
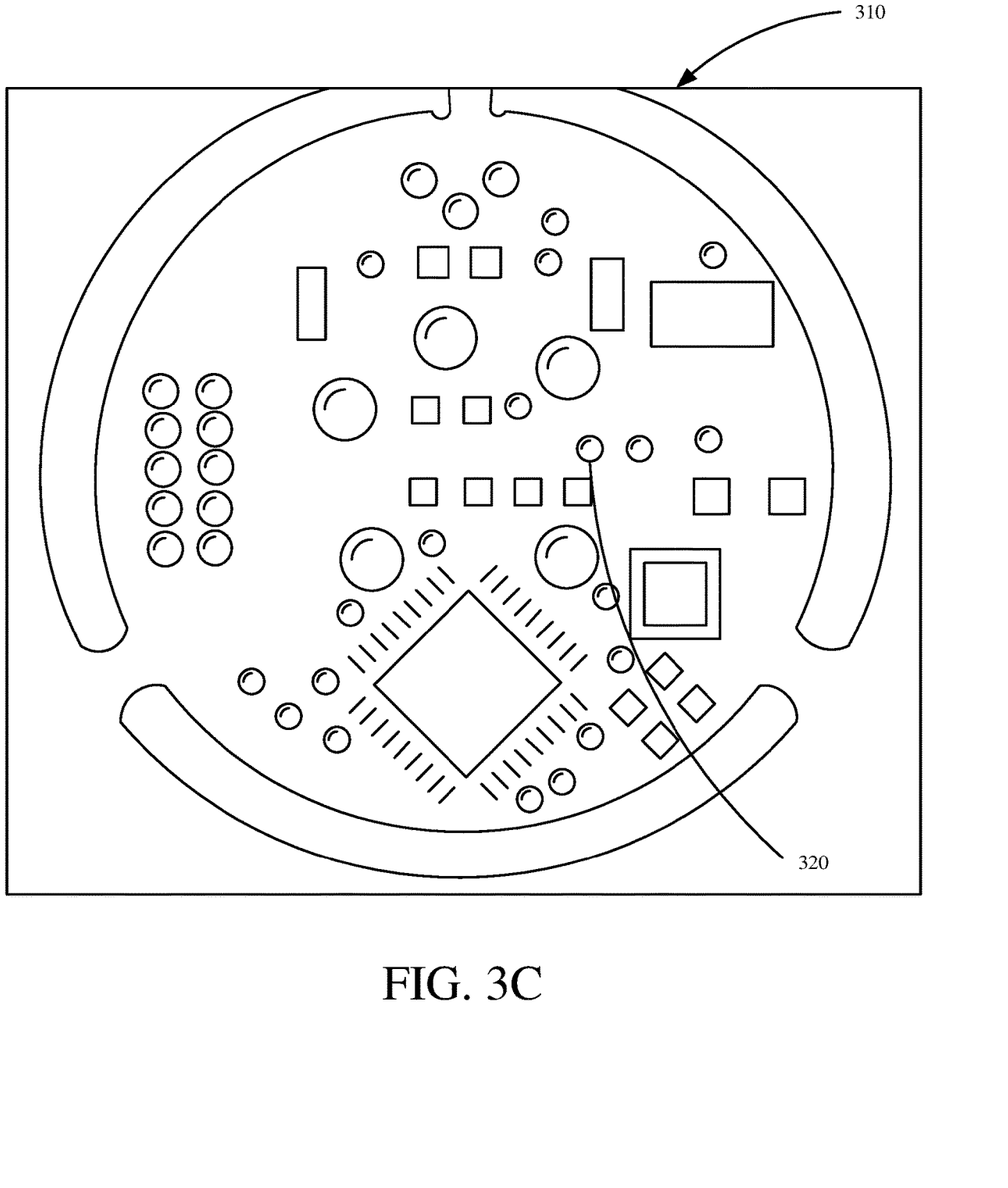

FIGS. 3A-3C illustrate a pressure transducing housing and circuitry in accordance with one embodiment of the present invention. FIG. 3A is a partial cutaway perspective view of housing 300, which includes a circuit card 310. Circuit card 310 comprises a switch 314 that is preferably a Hall Effect zero switch. Circuit card 310 also includes, a microprocessor 316. Circuit card 310 may include a factory interface header 312. Housing 300 is also configured to allow for a cable connector 302 to couple to circuit card 310. The use of a cable connector 302 can also enable wired process communication. Some embodiments provided herein allow for strain-relieved two-wire connections for compact cable interface.

FIG. 3B illustrates an enlarged cross-sectional view of housing 300, illustrating how circuit card 310 and associated components are arranged, in one embodiment. Walls of housing 300 are configured to couple to a base 330 that includes a pressure sensor disposed within module 340. Base 330 is metallic and preferably welded to module 340, for example using an existing sensor weld type. In the illustrated example, the pressure sensor is a solid-state strain gauge sensor. Microprocessor 316 is configured to read a pressure signal from a pressure sensor, such as sensor 104, via signal conditioning module 120 and provide a suitable output, such as a voltage output. Additionally, microprocessor 316 may be coupled to suitable communication circuitry to convey the measured pressure to another device via wired or wireless communication. Electronics within housing 300 can also be provided with user interface elements to allow a user or technician to perform one or more functions relative to a pressure transducer. For example, Hall Effect zero switch 314 may be configured such that, when a user places a magnet proximate an external surface of the housing, a zeroing function is performed for the transmitter. While a Hall Effect zero switch 314 is shown, in other embodiments additional switches can be placed in other locations to provide additional functionality. Further, the surface of housing 300 can be marked, or provided with surface indicia indicating that placement of a magnet proximate a particular location will actuate specific functions, such as zeroing the transducer.

As shown in FIG. 3B, the pressure transducer also includes a power chip 316. Power chip 316 may be coupled to or include a battery, such as a rechargeable battery. However, in embodiments where a transducer is coupled to a cable, for example using cable connection 302, power chip 316 may include suitable circuitry to condition power received from the cable for provision to other components within the pressure transducer, such as a microprocessor and/or communication circuitry. Some embodiments described herein provide wireless signaling (including NFC, Bluetooth LE, WIFI, WirelessHART®), and are powered from a battery coupled to power chip 316.

FIG. 3C is a top view of a circuit card 310. As illustrated in FIG. 3C, circuit card 310 comprises multiple through holes 320 configured to receive electrical connections and/or fluidic connections from a sensor module. As illustrated in FIG. 3C, the circuit card includes five through holes 320. However, it is to be understood that more or fewer through holes 320 could also be used, as well as in other arrangements. FIG. 3 illustrates one of through holes 320 that will pass a conductor of the pressure sensor module and allow a solder connection to be made directly from a sensor module to circuit card 310. Use of circuit card 310 provides for an exceptionally compact assembly. The compact assembly achievable using circuit card 310 in the arrangement shown allows for coupling of a transducer with circuit card 310 to a single-use reaction chamber while achieving highly accurate measurements.

Figure 4A:
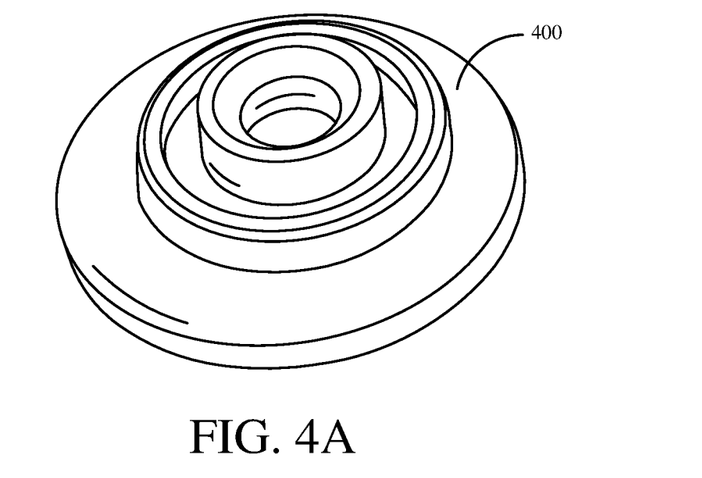
FIGS. 4A and 4B illustrate an example base portion in accordance with an embodiment of the present invention.
Figure 4B:
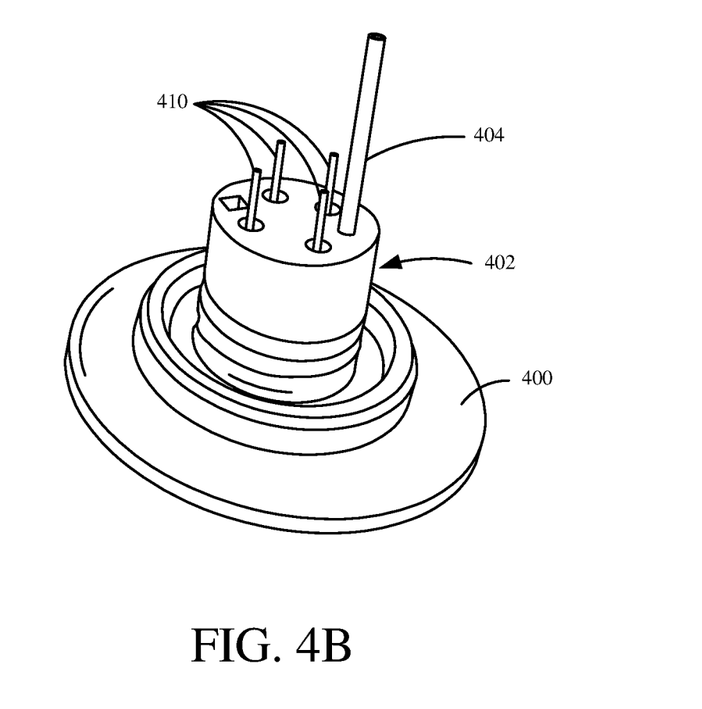

FIGS. 4A and 4B illustrate a base portion with an isolator diaphragm configured to be positioned against a diaphragm of a disposable connector in accordance with an embodiment of the present invention. Base portion 400 is a metallic base portion and includes an isolator diaphragm that is configured to be positioned against a corresponding polymeric diaphragm of a disposable connector. In the example shown in FIGS. 4A and 4B, base 400 is roughly 1.5 inches in diameter. However, embodiments of the present invention can be practiced with larger or smaller sizes, including, without limitation, base 400 being 0.75 inches in diameter.

Base 400 is presented in FIG. 4B, with a pressure sensor module 402 mounted thereto. As can be seen, pressure sensor module 402 includes a plurality of upwardly projecting features 410 and 404 which are configured to pass through the through holes of a circuit card, using, for examples, through holes 320 of circuit card 310. Feature 404 is a fluidic projection that can be used to provide a reference pressure to a solid-state pressure sensor module. Depending on the reference pressure, an overall indication of pressure from the pressure transducer can be presented as an absolute pressure, for example, in an embodiment where the reference pressure is a vacuum. The overall indication can also comprise a gauge pressure, for example, where the reference pressure is an atmospheric pressure. Additionally, other suitable indications of pressure can be provided, based on a different reference.

Figure 5:
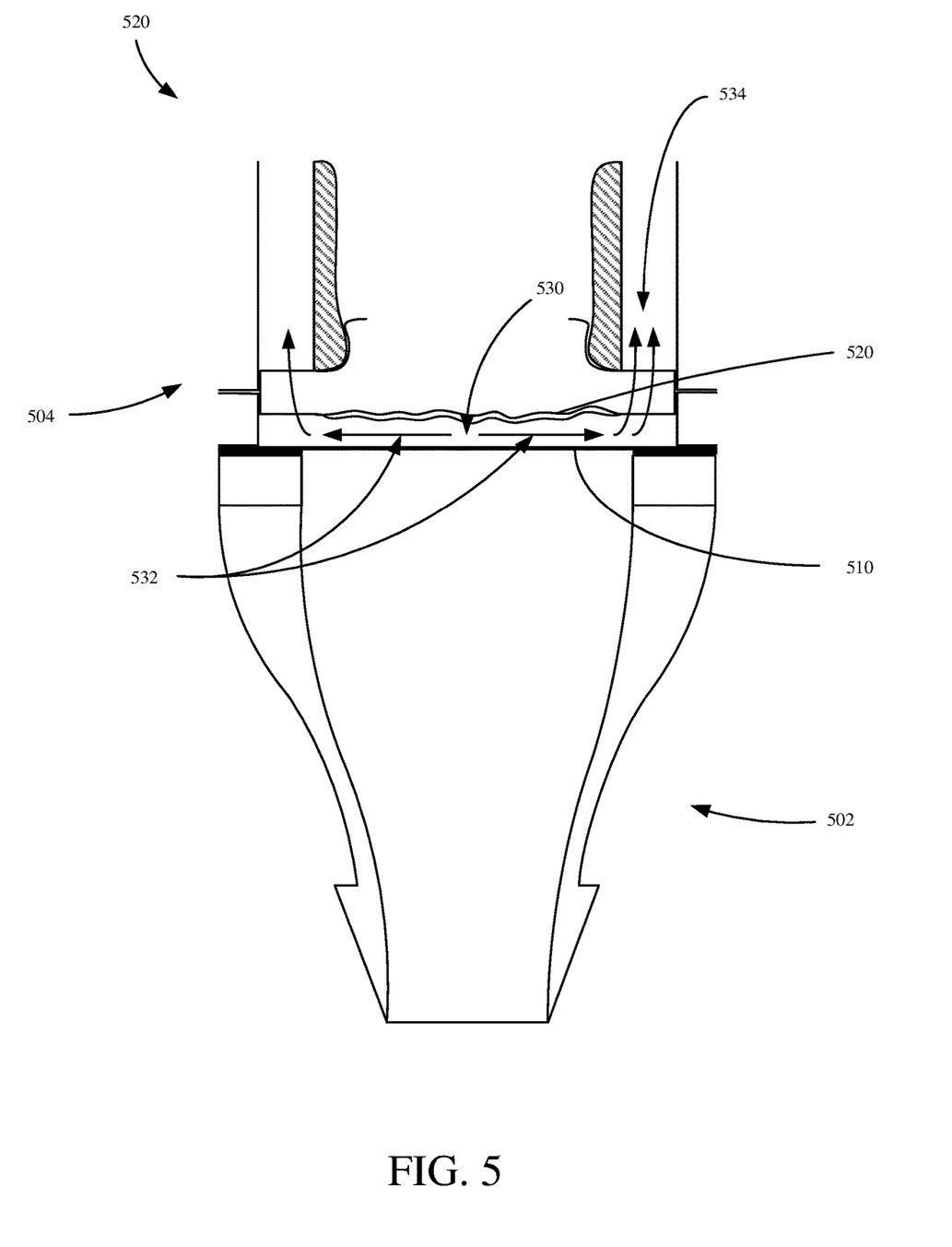
FIG. 5 is a diagrammatic view of a coupling between a pressure transducer and a disposable process connector in accordance with an embodiment of the present invention.

FIG. 5 is a diagrammatic view of a coupling between a pressure transducer and a disposable process connector in accordance with an embodiment of the present invention. In the example illustrated in FIG. 5, a metal diaphragm 520, of a transducer 504, has a convex shape, such that the center of diaphragm 520 first contacts the center of a polymeric diaphragm 510 of a process connector 502, as the two are brought together. The first coupling point is indicated by reference numeral 530. As a coupling proceeds, the contact area grows from center 530, as indicated by arrows 532. Air is forced radially outward during the coupling, reducing the likelihood of an air pocket developing and becoming trapped between diaphragms 510 and 520. Additionally, a vent hole 534 may be provided between the polymeric diaphragm 510, and isolator 520 to further facilitate air removal.

Figure 6A:
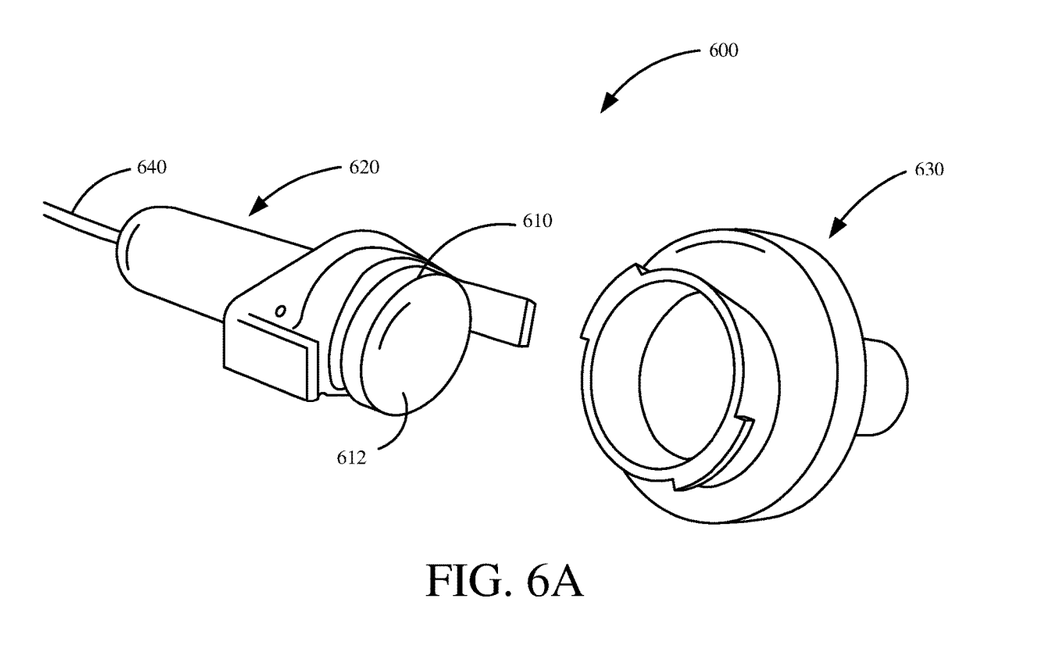
FIGS. 6A and 6B are perspective views of a compact pressure transducer and process connector in accordance with an embodiment of the present invention.
Figure 6B:
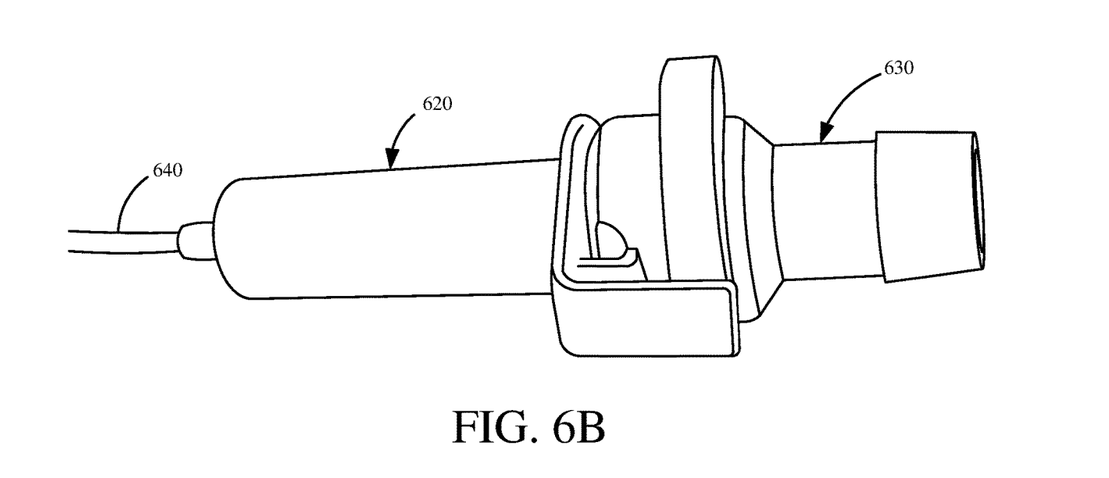

FIGS. 6A and 6B are perspective views of a compact pressure transducer and disposable process connector in accordance with an embodiment of the present invention. FIG. 6A illustrates a compact pressure transducer housing 620, decoupled from a disposable process connector 630, illustrating a metal base portion 610 and metal isolation diaphragm 612 coupled thereto. Transducer housing 620 is coupled to a cable 640, such that wired communication is enabled. In FIG. 6B, pressure transducer housing 620 is coupled to process connector 630. Diaphragm 612 is approximately 1 inch in diameter. However, in other embodiments, the tubing size and associated diaphragm diameter may be smaller, such as ½ inch diameter or even ⅜ inch diameter. A sensor can be integrated with sensor electronics, which also facilitates compensation for thermal fluctuations since a temperature sensor disposed on a circuit board is in relatively close proximity to the sensor. At least some embodiments described herein are configured to allow for direct coupling of a pressure transducer to a bioreaction chamber for highly accurate pressure readings.

Embodiments described herein may exhibit some of the following illustrative specifications associated with a compact pressure transducer. At least some pressure sensor transducers herein are useful over a pressure range of 0-40 psig (pounds per square inch gage), with a resolution of 0.005 psig, and an accuracy of 0.03 psig. Pressure transducers described herein may exhibit a less than 0.01 psig drift within a 21-day period and can be used in a temperature range between 5 to 50 degrees Celsius. Embodiments described herein can be configured to provide continuous sample rate, with temperature compensation. Full factory calibration can be accomplished with embodiments made from USP class VI material.

Figure 7:
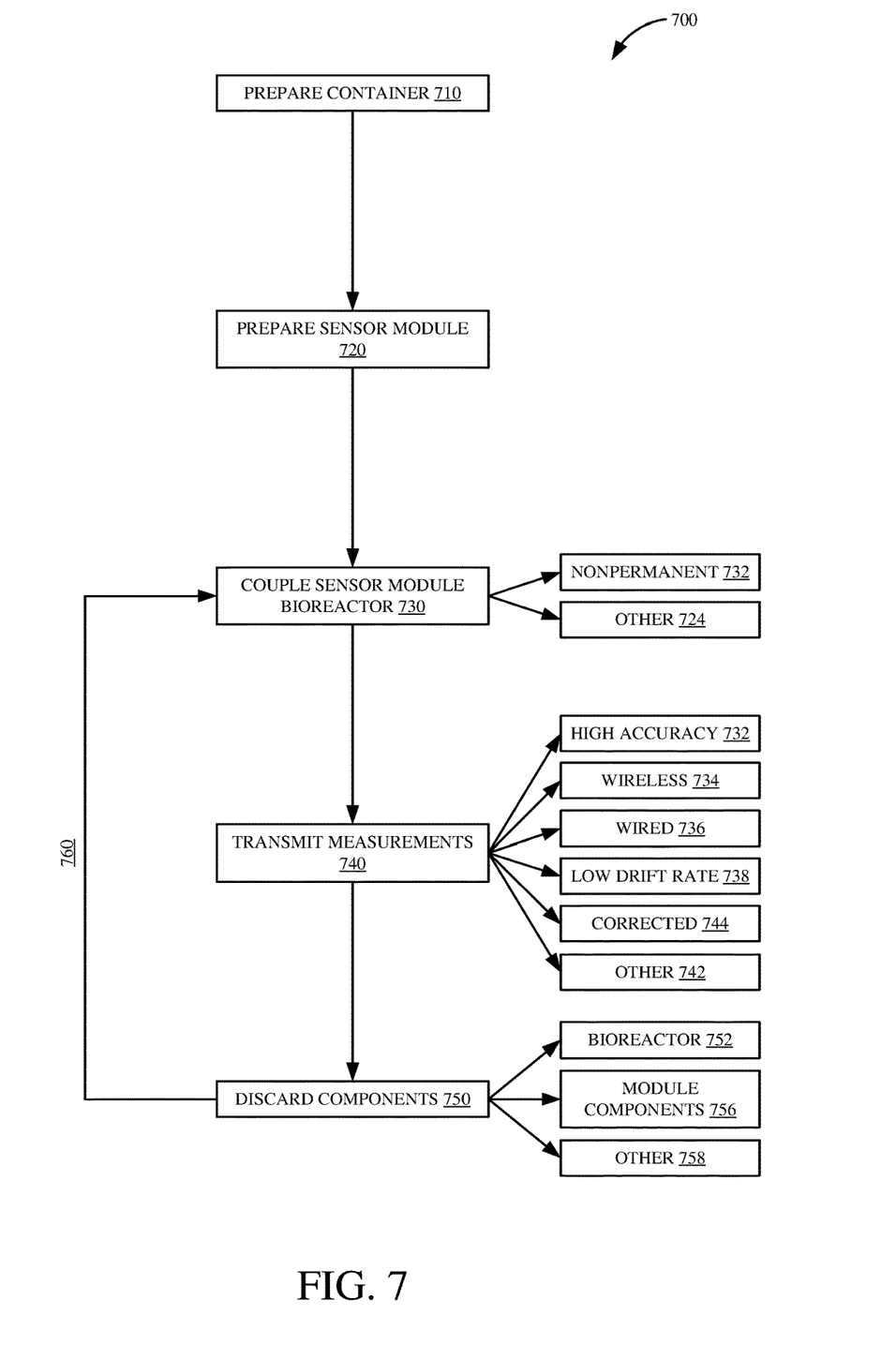
FIG. 7 is a flow diagram of a method of using a pressure transducer in accordance with an embodiment of the present invention.

FIG. 7 is a flow diagram of a method of using a pressure transducer in accordance with an embodiment of the present invention. Method 700 may allow for a pressure transducer to couple to a single-use container such that highly accurate pressure sensor module signals can be detected and communicated using a compact, pressure sensor transducer coupled to a disposable process connector, such as those described herein.

In block 710, a single-use container, such as a bioreactor, is prepared. For example, a single-use container is sterilized prior to use. However, in other instances, a sample may be introduced to the container to initiate a reaction.

In block 720, a transducer is prepared. For example, a pressure transducer can be prepared, as indicated in block 714. Preparation includes, assembly and calibration of a pressure transducer. Internally stored (non-volatile) calibration parameters are provided during a factory calibration, and can be made available with a certificate of accuracy. Calibration can also be verified by the end user as needed.

Preparation can also comprise removably coupling the pressure transducer to a disposable process connector. The pressure sensor module may comprise compact, single-use components configured to interface directly with the container.

In block 730, the pressure transducer is coupled to the single-use container. The coupling is a temporary coupling, as indicated in block 722. In another example, the coupling may be configured to last for the single-use of the container. Other couplings are also envisioned, as indicated in block 724. Some examples, as illustrated herein, comprise a fully integrated solution, with no additional equipment required such as a transmitter box in order to send signals to a control system.

In block 740, detected pressure measurements are transmitted. Compact pressure transducer provides high accuracy measurements, as indicated in block 732. Measurements can be transmitted wirelessly, as indicated in block 734, and/or through a wired communication loop, as indicated in block 736. Onboard digital correction of a pressure reading may be provided to account for thermal errors based on a signal from an integrated temperature sensor. At least some examples described herein provide accuracy better than 0.02 psi.

In block 750, components are discarded. Use of single-use components allows for reactions to proceed without the OP-infrastructure previously required. Additionally, accurate measurements can be obtained without the need for traditional mounted-in-place instruments previously required for sensitive pressure measurements. A single-use container can be discarded after use, as indicated in block 752.

As indicated by arrow 760, the pressure transducer is reusable, and coupled to a new disposable process connector, in order to monitor a reaction in additional single-use containers.

Figure 8:
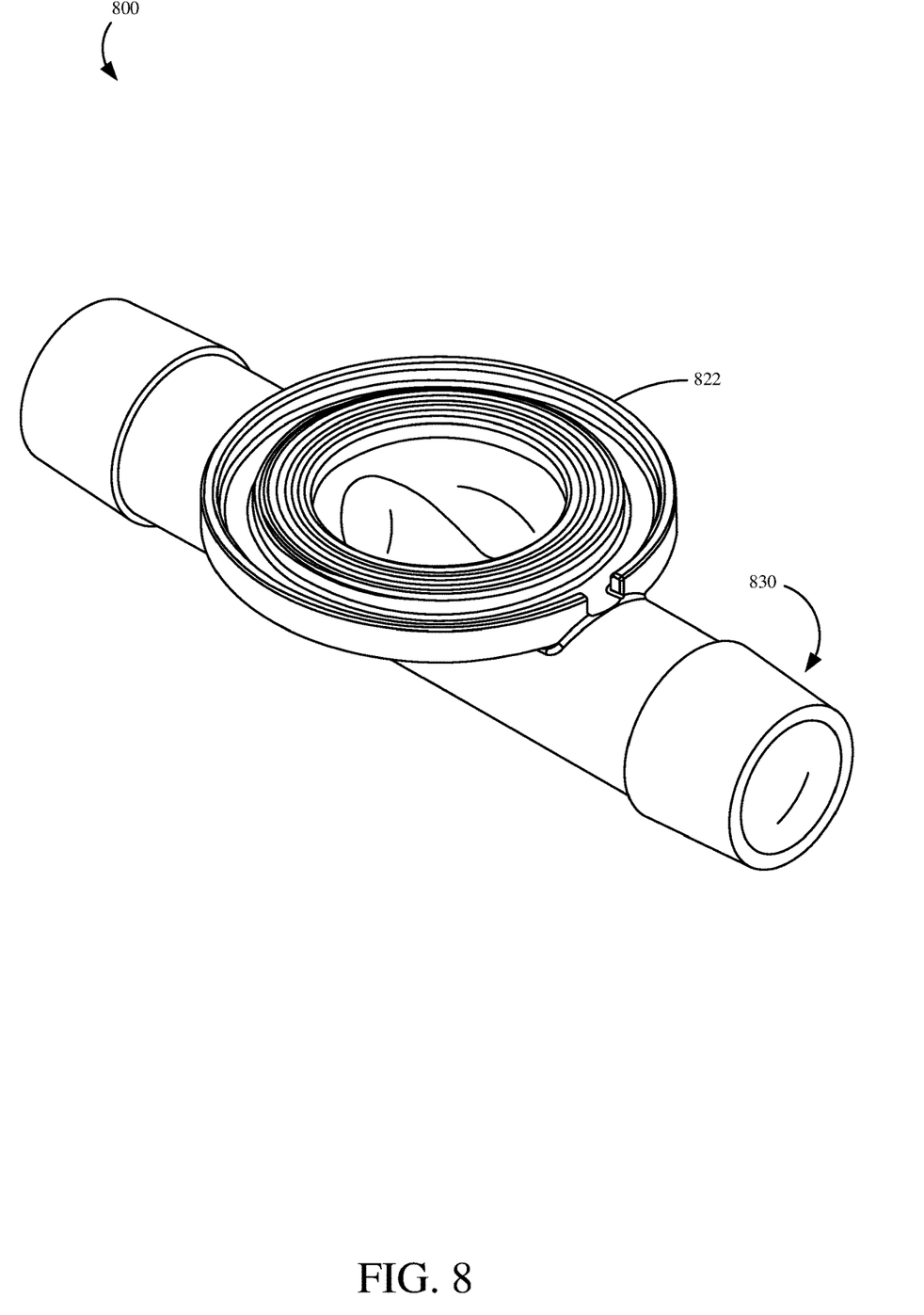
FIG. 8 is a diagrammatic view of a disposable process connector in accordance with another embodiment of the present invention.

FIG. 8 is a diagrammatic view of a disposable process connector in accordance with another embodiment of the present invention. Process connector 800 may, for example, be used with transmitter 200, or a similar transmitter, in an inline flow-through embodiment. For example, feature 822 may be configured to couple to feature 212 of transmitter 200.

A length of tubing (not shown) extends over fitting 830, which may be a hose barb fitting. Disposable process connector 800 has a polymeric diaphragm that provides a seal to the fluid flow path, but moves in response to pressure. The polymeric diaphragm of process connector 800 may be configured to contact diaphragm 226 of transducer 200.

Embodiments described herein provide a number of features that are believed to be highly useful to the life sciences field for monitoring pressure within, or associated with, a single-use vessel. Examples described herein provide a reusable pressure transmitter that can be coupled directly to a single-use vessel. The reusable pressure transmitter may provide a digitally processed pressure signal and/or employ an embedded microcontroller.

Systems described herein exhibit high stability, with drift less than 0.01% FS per year. Integrated transducers described herein can be produced in a lightweight fashion, for example roughly 2-3 ounces in weight, while providing high accuracy. Polymeric housings described herein allow for lightweight and wireless signal penetration. Additionally, isolators are designed to be very sensitive and flat to better interface with the polymer barrier for single-use applications.

Embodiments described herein can be used for headspace applications, inline pressure measurement applications, flow fittings, et cetera. Additionally, while embodiments described herein have been focused on a single-use container or vessel, it is expressly contemplated that other fields and industries may benefit from embodiments of the present invention, such as the medical field. Additionally, other process connections could allow a lightweight pressure transducer to mount directly to flexible tubing, piping or any number of other process interfaces and remain unsupported (no additional mounting hardware required). A lightweight property and potential wireless communication could allow pervasive sensing applications on a much smaller scale.

Although the present invention has been described with reference to preferred embodiments, workers skilled in the art will recognize that changes may be made in form and detail without departing from the spirit and scope of the invention.

What is claimed is:

1. A pressure-sensing system comprising:
   a single use container;
   a disposable process connector configured to couple to the single-use container, the disposable process connector having a deflectable diaphragm; and
   a pressure transducer, removably coupled to the disposable process connector, comprising:
   an isolation diaphragm positioned adjacent the deflectable diaphragm of the disposable process connector;
   a pressure sensor module operably coupled to the isolation diaphragm;
   a controller coupled to the pressure sensor module and configured to transmit a detected indication of pressure within the single-use container.

2. The pressure sensing system of claim 1, wherein the pressure transducer comprises a circuit card configured to couple to the pressure sensor module containing a pressure sensor.

3. The pressure sensing system of claim 1, wherein the disposable process connector is an inline flow-through connector.

4. The pressure sensing system of claim 1, wherein the disposable process connector is configured to coupled directly to the single-use container.

5. A pressure transducer for a single-use container, the pressure transducer comprising:
   a polymeric housing;
   a base having an isolation diaphragm;
   a sensor module coupled to the base, the sensor module having a pressure sensor operably coupled to the isolation diaphragm; and
   circuitry disposed within the polymeric housing and coupled to the pressure transducer, the circuitry comprising a microprocessor configured to obtain a pressure measurement from the pressure sensor and provide an output signal based on the measured pressure.

6. The pressure transducer of claim 5, wherein the pressure sensor is a strain gauge pressure sensor.

7. The pressure transducer of claim 5, wherein the circuitry comprises a Hall-Effect switch.

8. The pressure transducer of claim 7, wherein the Hall-Effect switch is configured to generate a user-initiated function.

9. The pressure transducer of claim 8, wherein the function is a zeroing of the transducer.

10. The pressure transducer of claim 5, wherein the transducer comprises a cable connector configured to enable wired process communication.

11. The pressure transducer of claim 5, wherein the circuitry further comprises a communication module coupled to the microprocessor and configured to transmit the output signal in accordance with a wireless protocol.

12. The pressure transducer of claim 5, wherein the communication module is configured to provide the output signal using a 4-20 mA communication loop.

13. The pressure transducer of claim 5, wherein the communication module is configured to provide the output signal using a voltage output.

14. The pressure transducer of claim 5, wherein the communication module is configured to provide the output signal using a digital communication loop.

15. The pressure transducer of claim 5, wherein the circuitry comprises an analog-to-digital converter operably disposed between the pressure sensor and the microprocessor.

16. A method of using a pressure transducer with a single-use container, the method comprising:
   mounting a disposable process connector directly to the single-use container;
   operably coupling the pressure transducer to the disposable process connector;
   measuring a pressure within the single-use container with a pressure sensor in the pressure transducer;

providing an output to a remote device based on the measured pressure; and wherein the pressure transducer comprises a first diaphragm, the disposable process connector comprises a second diaphragm, and wherein operably coupling the pressure transducer to the disposable process connector comprises operably coupling the first diaphragm to the second diaphragm such that air is forced radially outward.

17. The method of claim 16, wherein coupling the pressure transducer to the disposable process connecter also comprises forcing air through a vent hole.

18. The method of claim 16, wherein coupling the pressure transducer to the process connecter comprises a removable coupling such that the pressure transducer is reusable with additional disposable process connectors.

* * * * *

UNITED STATES PATENT AND TRADEMARK OFFICE
CERTIFICATE OF CORRECTION

PATENT NO. : 10,584,309 B2
APPLICATION NO. : 15/603932
DATED : March 10, 2020
INVENTOR(S) : Paul R. Fadell, Michael Knopf and Jay I. Scheldorf Page 1 of 1

It is certified that error appears in the above-identified patent and that said Letters Patent is hereby corrected as shown below:

In the Claims

Claim 4, Line 17, "coupled" should read "couple"

Signed and Sealed this
Thirtieth Day of March, 2021

Drew Hirshfeld
*Performing the Functions and Duties of the
Under Secretary of Commerce for Intellectual Property and
Director of the United States Patent and Trademark Office*